United States Patent
Kyriakou

(10) Patent No.: US 9,295,440 B2
(45) Date of Patent: Mar. 29, 2016

(54) METHOD FOR RECORDING AND DISPLAYING AT LEAST TWO 3D SUBTRACTION IMAGE DATA RECORDS AND C-ARM X-RAY APPARATUS

(71) Applicant: Yiannis Kyriakou, Spardorf (DE)

(72) Inventor: Yiannis Kyriakou, Spardorf (DE)

(73) Assignee: SIEMENS AKTIENGESELLSCHAFT, München (DE)

( * ) Notice: Subject to any disclaimer, the term of this patent is extended or adjusted under 35 U.S.C. 154(b) by 173 days.

(21) Appl. No.: 13/740,307

(22) Filed: Jan. 14, 2013

(65) Prior Publication Data

US 2013/0188771 A1 Jul. 25, 2013

(30) Foreign Application Priority Data

Jan. 19, 2012 (DE) .................. 10 2012 200 715

(51) Int. Cl.
*A61B 6/00* (2006.01)
*A61B 6/03* (2006.01)

(52) U.S. Cl.
CPC .............. *A61B 6/481* (2013.01); *A61B 6/032* (2013.01); *A61B 6/4441* (2013.01); *A61B 6/504* (2013.01); *A61B 6/5205* (2013.01); *A61B 6/4085* (2013.01)

(58) Field of Classification Search
CPC .......... A61B 6/03; A61B 6/032; A61B 6/481; A61B 6/488; A61B 6/503; A61B 6/504; A61B 6/507
USPC ...................................................... 378/98.12
See application file for complete search history.

(56) References Cited

U.S. PATENT DOCUMENTS

| | | | | |
|---|---|---|---|---|
| 5,852,646 | A * | 12/1998 | Klotz et al. | 378/8 |
| 6,233,308 | B1 * | 5/2001 | Hsieh | 378/62 |
| 7,474,727 | B2 | 1/2009 | Lauritsch | |
| 7,852,984 | B2 * | 12/2010 | Zellerhoff | 378/98.12 |
| 7,899,151 | B2 * | 3/2011 | Boese et al. | 378/17 |
| 7,986,762 | B2 * | 7/2011 | Kunze | 378/11 |
| 8,676,297 | B2 * | 3/2014 | Benndorf et al. | 600/425 |
| 2007/0206724 | A1 * | 9/2007 | Sakaguchi et al. | 378/62 |
| 2007/0232901 | A1 * | 10/2007 | Benndorf et al. | 600/425 |

FOREIGN PATENT DOCUMENTS

DE 102006012181 A1 9/2007

OTHER PUBLICATIONS

Feldkamp et al.; Practical Cone-beam Algorithm JOSA A1, 612 (1984) J. Opt. Soc. Amer. A, vol. 1, No. 6, Jun. 1984, pp. 612-619; Journal of the Optical Society of America; Magazine; 1984.

(Continued)

*Primary Examiner* — Thomas R Artman

(57) ABSTRACT

A method for recording at least two 3D subtraction image data records with a C-arm x-ray apparatus is provided. A mask run is implemented with a rotation angle of at least 180° plus fan angle plus an additional angle, while projection image data record of a native 3D image data record are recorded. A filler run is implemented after administration of a contrast agent with a rotation angle of at least 180° plus fan angle plus an additional angle. Partial 3D image data records are generated and formed into a set of projection image data records. Each set of projection image data records is reconstructed, wherein a 3D subtraction image data record is generated by subtracting data of a native 3D image data record from data of a 3D image data record after the administration of the contrast agent.

15 Claims, 5 Drawing Sheets

(56) References Cited

OTHER PUBLICATIONS

Ludwig Ritschl et al., Improved Sparsity-Constrained CT Image Reconstruction Applied to Clinical Data, IEEE MIC 2010, Knoxville, USA.; Others; 2010.

Ludwig Ritschl et al., Improved Sparsity-Constrained Image Reconstruction Applied to Clinical CT Data, IEEE Nuclear Science Symposuim&Medical Imaging Conference(201 0), pp. 3231-3240; Others; 2010.

* cited by examiner

FIG 2
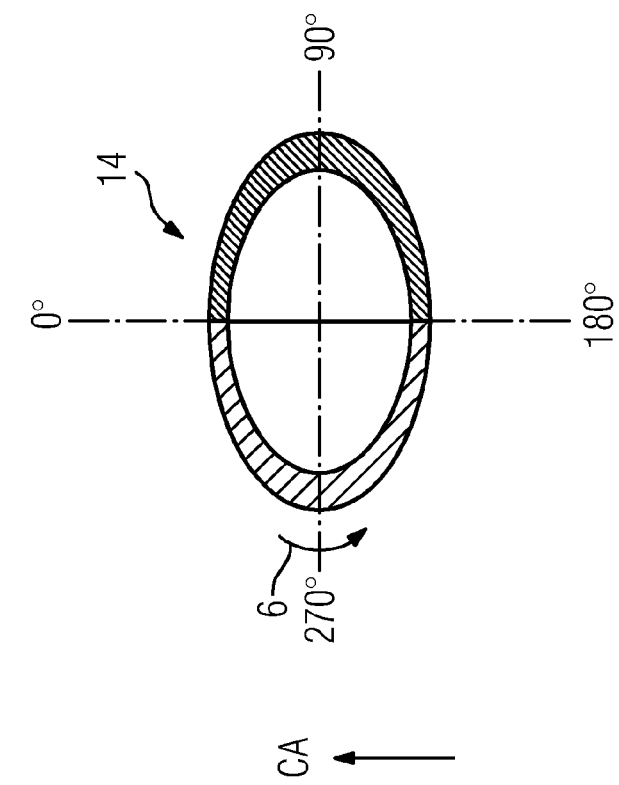
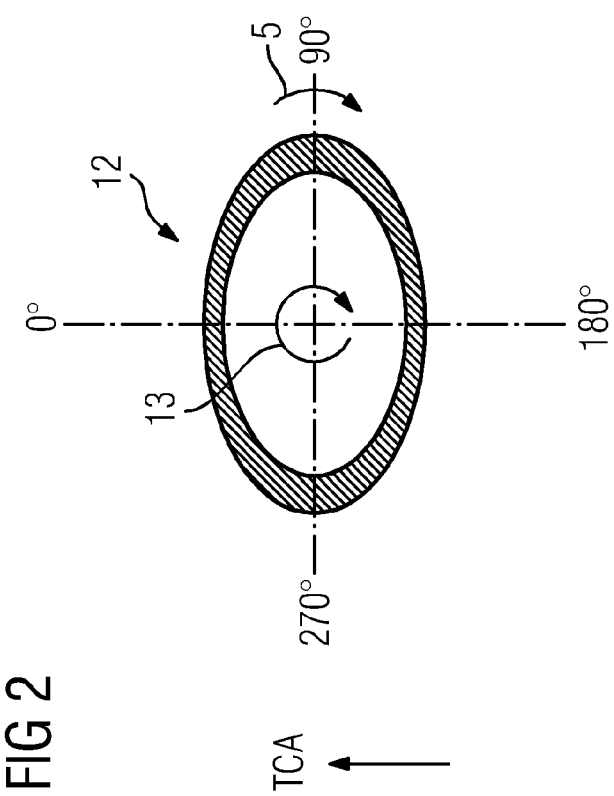

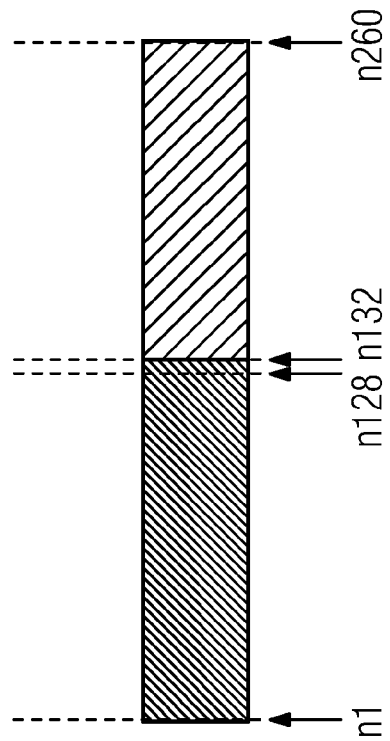
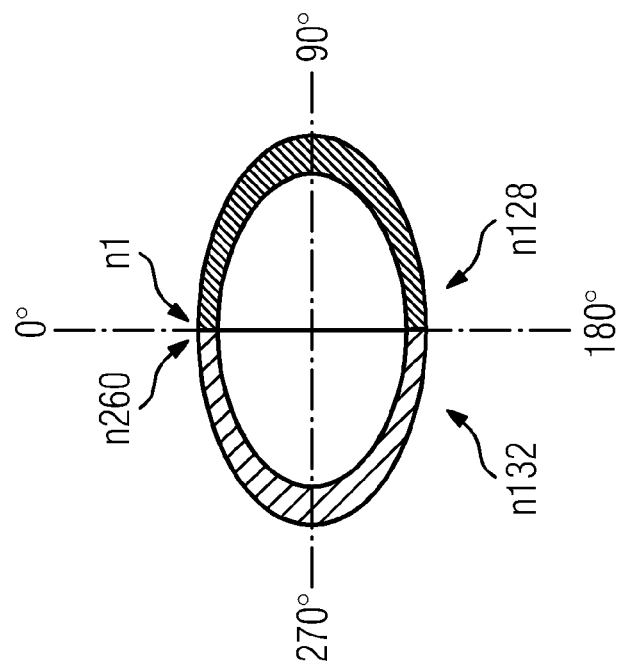
FIG 3

METHOD FOR RECORDING AND DISPLAYING AT LEAST TWO 3D SUBTRACTION IMAGE DATA RECORDS AND C-ARM X-RAY APPARATUS

CROSS REFERENCE TO RELATED APPLICATIONS

This application claims priority of German Patent Application No. 10 2012 200 715.6 DE filed Jan. 19, 2012. All of the applications are incorporated by reference herein in their entirety.

FIELD OF INVENTION

A method for recording and displaying at least two three-dimensional (3D) subtraction image data records consisting of at least one native 3D image data record and at least one 3D image data record recorded following administration of a contrast agent is provided, which display at least one part of the vascular system of a patient, by means of a C-arm x-ray apparatus, wherein the 3D image data records are obtained in each instance from a predetermined number of two-dimensional (2D) projection image data records.

BACKGROUND OF INVENTION

With the previously known three-dimensional vascular representation, a so-called mask run and a filler run are recorded. With the "mask run", the C-arm of the C-arm x-ray apparatus rotates about the body part of the patient or the entire patient and records a first sequence of x-ray images (2D projection image data records) through the predetermined angular range without contrasting. Contrast agent is then injected into the vessel of interest and a second sequence of x-ray images is recorded with a renewed C-arm rotation, the so-called "filler run". The two sequences are now subtracted from one another such that only the contrasted vessels (i.e. containing contrast agent) are still visible in the result. These are now reconstructed using a 3D reconstruction method to form a three-dimensional image data record. Alternatively, mask and filler run sequences can also be reconstructed separately from one another and the resulting three-dimensional data records can be subtracted from one another. Both the mask run and also the filler run are subsequently referred to as "rotation run". With a rotation run for recording a 3D image data record, 120 to 140 projection image data records are usually recorded in each instance through a rotation angle of 200° of the C-arm of the C-arm x-ray apparatus as raw data and reconstructed to form a 3D image data record.

Here the recording of the projection image data records of a 3D image data record requires approximately 4 to 5 seconds, wherein the recording duration of the native 3D image data record is non-critical. The arterial phase of the contrast agent bolus, in other words the duration of stay of the contrast agent in the arterial vessels, is only however approximately 3 seconds. The contrast agent is subsequently transported via the capillary blood vessels into the veins. With the known recording method, it is therefore not possible to record sufficient projection image data records during the arterial phase in order to obtain separate, three-dimensional image data records of the arteries and the veins in each instance.

In order to solve this problem, DE 10 2006 012 181 A1 discloses implementing a number of rotation runs following the administration of a contrast agent in each instance, wherein the point in time of the administration of the contrast agent varies in comparison with the starting point in time of the recording data. Subsequently, those image data records recorded during the arterial phase from the recorded projection image data records for instance are selected in order to obtain a projection image data record for each required projection angle in order to be able to create a 3D image data record which was reconstructed from projection image data records, which represent the vascular system for the examined patient during the arterial phase. A three-dimensional image of the arteries of the patient is consequently obtained.

This method is disadvantageous in that a contrast agent has to be administered a number of times. Since the contrast agent remains in the vascular system throughout a time frame of several minutes, this may result, since it is increasingly distributed, in a deterioration of the contrast between a given contrast agent bolus and the fluid present in the vascular system.

SUMMARY OF INVENTION

It is an object to specify a method for recording subtraction image data records, which enable the recording of the arterial and the venous phase during just one single administration of the contrast agent. A method as claimed in the claims is proposed in order to solve this problem.

In order to solve this problem, it is proposed to render possible a series of 3D subtraction image data records by recording a series of projection image data records with a greater data density than provided with standard measurements throughout a large rotation angle up to a maximum rotation angle 360° using the so-called "sliding window" technique. In this way sufficient projection image data records are firstly recorded prior to the administration of the contrast agent, e.g. 260 projection image data records with a rotation angle of the C-arm of 360°. Following administration of the contrast agent, 260 projection image data records are similarly recorded with a rotation angle of the C-arm of 360°. In order to prevent complicated post-processing steps, a native corresponding projection image data records recorded at the same projection angle and recorded prior to administration of the contrast agent exists for each projection image data record recorded following administration of the contrast agent. The first (e.g. 132) projection image data records following administration of the contrast agent are the set of data which covers a rotation angle of 180° plus fan angle and therefore allow for the reconstruction of a 3D image data record. When the projection image data records are recorded equidistantly, i.e. with in each instance the same rotation angle between two projection image data records, the necessary rotation angle is always covered when using 132 consecutive projection image data records. Accordingly, 3D image data records and subtraction image data records can be produced from the 260 projection image data records.

The additional angle depends here on the number of projection images to be recorded. With 120 projection images to be recorded, one possible recording density is above 180° rotation angle, the rotation angle at least to be recorded amounts to 180° plus fan angle, in other words approximately 200°. This corresponds for instance to a minimal number of 132 projection image data records. In order to be able to achieve a minimal "sliding window", at least one further projection image is to be recorded, wherein an equidistant distribution of the projection image data record is useful. The additional angle then amounts to:

Additional angle=minimal rotation angle/minimal number of exposures*number of further projection images With the afore-described recording density, a value of 200°/132=1.5° results for instance. A rotation of 1.5° is to be provided between the recordings of consecutive projection images. The additional angle amounts for instance to between 20° and 160° depending on the number of further projection images to be recorded. The number of further projection images to be recorded is determined by the number of projection images to be recorded minus the minimal number of projection image data records, wherein at 160° approximately the maximum rotation angle of 360° is achieved, preferably 50° to 140°.

It is apparent that the described numerical values are purely exemplary and a higher number of projection image data records and a smaller rotation angle than 360° can also be used in particular.

The particular advantage of the method lies in a plurality of 3D subtraction image data records being generated at any phase of the contrast agent bolus. It is herewith particularly possible, in the event of abnormalities such as AV shunts or AV functional interferences, to always generate a 3D subtraction image, which exclusively displays veins and also a subtraction image which exclusively displays arteries. These can then be shown separately or overlaid and/or using color coding. It is also possible, particularly with interventional operations, to display the vessels in a projected manner on two-dimensional image data records. The overlaid or color-coded displays are in this way not restricted to the display of the purely arterial or venous phase, but each reconstructed 3D image data record can instead be displayed at any phase of the image data recording. Here the single administration of the contrast agent is in particular sufficient to generate the 3D image data records of the arterial and venous phase.

The direction of rotation of the C-arm of the C-arm x-ray apparatus can preferably be changed following a rotation run and prior to the next rotation run. If the scanning direction of the projection image data records of the native 3D image data record is in the clockwise direction, the scanning direction of the first 3D image data record is therefore counter clockwise following administration of the contrast agent. Waiting times can therefore be avoided between recordings of several 3D image data after administration of the contrast agent.

At least two or three filler runs can advantageously be implemented following a single administration of contrast agent. In other words, the filler run includes a number of rotations of the C-arm, e.g. a forward and backward run. This is of particular interest with a pathologically extended or delayed venous phase. The projection image data records of the filler runs can be acquired with the same or also with deviating, preferably low, recording density, such as the mask run. A lower recording density is advantageous in that the filler runs can be implemented with a faster movement of the C-arm and thus in shorter time span than the mask run. In this way attention should however be paid to corresponding projection image data records being provided in the mask run at the angular positions of the projection image data records of the filler run. As a result, during the subtraction, there is the choice of either subtracting the projection image data records corresponding to one another from the filler and mask run, or deducting the reconstructed 3D image data records from one another.

When recording a number of 3D image data records following administration of the contrast agent, a change in the scanning direction or rotation direction is preferably also performed during the recording, in order to be able to prevent the C-arm from moving back to a fixed starting position and thereby certain measuring pauses.

At least three 3D image data records can be particularly advantageously recorded following administration of the contrast agent. In this way, more 3D image data records are required with a small overall rotation angle for a 3D image data record of for instance just above 180° in order to cover the complete contrast agent passage than with a rotation angle of 360°. In particular, it is possible to record so-called half scans. Here only 180° plus fan angle is covered during the rotation of the C-arm. Three filler runs are preferably acquired during this type of recording. A rapid data recording is possible with half scans.

A rotation angle of at least 270° can preferably be used to record a 3D image data record and at least 180 projection image data records can be recorded.

Alternatively, a rotation angle of 360° can be used to record a 3D image data record and at least 240 projection image data records can be recorded.

Alternatively, a rotation angle of 360° can be used to record a 3D image data record and at least 260 projection image data records can be recorded.

The higher the number of recorded projection image data records, the more precise the arterial and venous phases can be separated from the mixed phase disposed there between. In this way, the entire number of images which can be recorded is determined from the ability of the contrast agent bolus to display in the projection image data records and the measuring time limited thereby. This measuring time can be invested for instance in four 3D image data records with a rotation angle of 220° at 130 projection image data records or in two 3-D-image data records with a rotation angle of 360° and 260 projection image data records. The selection depends here on the AV parameters.

A biplanar C-arm x-ray apparatus can advantageously be used. Biplanar C-arm x-ray apparatuses enable image data to be recorded in a shorter time span on account of the additional image generation unit. As a result, the temporal resolution can be increased and an improved separation of the arterial and venous phase can be achieved. The rotation angle used is smaller here than with a monoplanar system, namely up to 180° instead of a maximum of 360°. A larger angle is however effectively scanned on account of the angular spacing of the imaging units.

A C-arm x-ray apparatus with a stationary foot can preferably be used. A C-arm x-ray apparatus firmly fixed to the ground is understood here by the term stationary foot. The C-arm x-ray apparatus of this type likewise enables shorter measuring times, since they enable higher rotation speeds. Recordings with a rotation of 360° in 4 s can be implemented with a stationary foot. Therefore patients with short AV cycles can also be recorded for instance on account of AV shunts, in which the arteries and the veins can be displayed separately.

The 3D image data records can advantageously be reconstructed from the respective projection image data records using the Feldkamp algorithm with Parker weighting. The Feldkamp algorithm represents a known method for reconstruction of 3D image data records, which are obtained from projection image data records. The overvaluation of repeatedly measured positions in the examination object is prevented with the Parker weighting.

With the filler run(s), a delay between injection of the contrast agent and the start of the rotation run can either be set automatically or manually. The delay should be exactly the time which the bolus requires to advance from the injection site (intravenously or intra-arterially) to the part of the vascular tree of interest. Empirical values or standard settings can either be used here or the delay can be determined by means of a test bolus and 2D DSA.

In order to be able to take unconventional delay times of the bolus into account, which may occur particularly with vascular diseases such as AVM (Arteriovenous malformations), it is advantageous to provide a test bolus at the same injection site prior to recording of the filler run(s) and to observe the passage of the test bolus by means of 2D DSA (two-dimensional digital subtraction angiography). In this way projection images are recorded from a viewing angle with high temporal resolution, these are each subtracted with a native projection image and the inflow of the bolus is observed. A suitable delay time can be determined herefrom between injection and start of the filler run(s). Furthermore, a suitable rotation speed of the C-arm and recording density, as well as a suitable angle of rotation can also be determined with the test bolus.

It is also possible to observe the inflow of the contrast agent bolus manually on projection images recorded and displayed in real time, so-called fluoroscopy images and to manually start the filler run if the bolus begins to flow into the area of interest.

The 3D subtraction image data records can be shown overlaid with 2D fluoroscopy images in the representation according to a preferred embodiment as a 3D overlay or 3D road mapping. In this way, the display of various 3D subtraction image data records one behind the other enables the impression to be produced as if certain parts of the vascular structure were switched on or off. Alternatively, the 3D subtraction image data records may also be displayed without overlay in the Cine Mode, in other words in a sequence, as a result of which the temporal path of the contrast agent bolus through the vascular structure can in turn be effectively visualized.

Optionally the mask run or combinations of the mask and filler run can be used as advance information for advanced reconstruction techniques, in particular iterative reconstruction techniques for reducing artifacts and when reconstructing from smaller rotational angles, as described for instance in *Improved Sparsity Constrained CT Image Reconstruction Applied to Clinical Data* by Ludwig Ritschl et al., IEEE MIC 2010.

A recording phase can advantageously be introduced during the recording of the projection image data of at least one filler run. The further recording of the projection image data can be started manually or automatically. The recording phase is used to optimize the recoding of extreme pathologies and extreme deviations associated therewith from the AV parameters which are usually present. In particular, the recording phase can take place with a projection angle of 200° of the first filler run, preferably in other words after recording the projection images of a complete 3D image data record, which maps the arterial phase. The time instance of the recording phase can be optimally determined as a function of the afore-described test bolus.

The 3D subtraction images are preferably generated in the image frame, i.e. the reconstructed 3D image data record of the mask run is deducted from a reconstructed 3D image data record of a filler run. The 3D image data records can be registered prior to the subtraction. The subtraction consequently takes place after registering the 3D image data records.

In addition, a C-arm x-ray apparatus is provided which is characterized in that it is embodied to implement the afore-described method.

BRIEF DESCRIPTION OF THE DRAWINGS

FIG. 2 shows a flow diagram of the method in a first embodiment,
FIG. 3 shows a flow diagram of the method in a second embodiment.

DETAILED DESCRIPTION OF INVENTION

Figure 1:
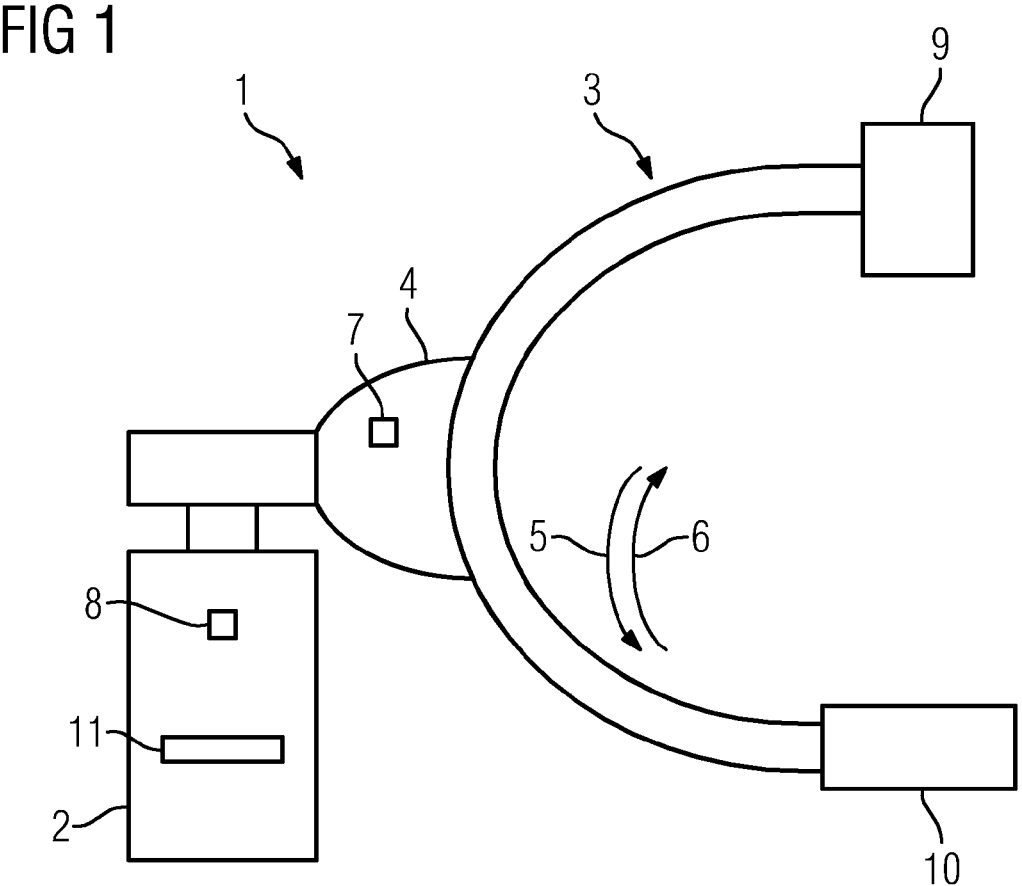
FIG. 1 shows a C-arm x-ray apparatus.

FIG. 1 shows a C-arm x-ray apparatus 1 with a supporting apparatus 2 and a C-arm 3. The C-arm 3 is connected to the supporting apparatus 2 via the suspension 4. To record data, the C-arm, 3 can be moved in the direction of the arrows 5 and 6 by means of a motor 7 found in the suspension 4. A control apparatus 8 for activating the motor 7 in the suspension 4 and for controlling the x-ray source 9 and the detector 10, which are arranged on the ends of the C-arm 3, is disposed in the supporting apparatus 2. The generator 11 for high voltage is further accommodated in the supporting apparatus 2.

The control apparatus 8 naturally also includes a storage unit for storing the recorded data. It may also comprise a computing facility for further processing the recorded data and a display apparatus. The recorded data may however also be further processed on an external computing facility.

Aside from the rotation directions shown in the direction of the arrows 5 and 6, the C-arm 3 can still be moved vertically and about further axes, in order to enable a precise positioning of the patient in the isocenter. These corrections can naturally also be performed within the scope of the method.

FIG. 2 shows a flow diagram of the method in a first embodiment. Here the patient-specific waiting time P between administration of the contrast agent and mapping of the contrast agent in the recording area of interest is determined as the first step. To this end, a native two-dimensional projection image of the area to be examined is recorded, a test bolus (TCA: test contrast agent) is provided and subsequently several projection images of the area of interest are in turn recorded. The test bolus differs from the subsequently occurring administration of the contrast agent only in that a smaller quantity is administered. Subtraction images are determined from the native projection image and the projection images recorded following administration of the test bolus, with the aid of which the waiting time can he automatically determined for instance by means of use of a signal threshold value.

This first step is nevertheless optional; a standard value can also be used instead. The use of a test bolus to determine the waiting time can take place in all described embodiments. In particular, the rotation speed of the C-arm 3 can be adjusted by means of the thus determined time value.

As a second step, 240 native projection images 12 are acquired via a rotational angle 13 of the C-arm 3 of 360°. The number of projection images 12 may lie in a range of 150 to 360, with 240 an optimum amount of necessary information content is however provided by comparison with the applied radiation dose. All angles above 180° plus fan angle are essentially taken into consideration as rotation angle 13, but the use of the complete rotational movement of the C-arm 3 of the C-arm x-ray apparatus 1 facilitates the distinction between the arterial and venous phase. The rotation takes place in the direction of the arrow 5.

After recording the native 3D image data record, the contrast agent (CA) is applied intra-arterially and the data recording is started after the waiting time determined either by means of the test bolus or after a standard waiting time. In this way the rotation of the C-arm 3 starts at the position or at least in the vicinity of the position at which the C-arm 3 is located after recording the native 3D image data record. Accordingly, the C-arm 3 rotates in the direction of the arrow 6. In this way at least 150 projection image data records 14 are recorded following administration of the contrast agent, in particular 240. In order to simplify the data processing, the projection image data records 14 are recorded following administration of the contrast agent at the same angular position, at which the projection image data records 12 of 3D image data record were recorded. As a result, the individual projection image data records 12 and 14 can be directly subtracted from one another with a corresponding projection angle in each instance and without further calculations. The number of projection image data records of the 3D image data records following administration of the contrast agent has the same maximum here as the number of projection image data records of the native 3D image data record.

After the data recording, the corresponding projection image data records 12 and 14 are subtracted from one another as raw data and 132 associated subtraction images are reconstructed in each instance to form a 3D subtraction image by means of the Feldkamp method with Parker weighting described by Feldkamp et al. in Practical Cone-beam Algorithm, and published in Journal of the Optical Society of America, Vol. 1, No. 6, Jun. 1984, pages 612 to 619. In this way, the associated subtraction images must include a rotation angle of 180° plus fan angle in each instance. This type of reconstruction is also referred to as "sliding window technique". The number of subtraction images used may naturally also be higher, as long as not all existing subtraction images are used, a "sliding window" is possible.

The two can then be selected from these 3D subtraction image data records, which indicate the vessels of the recorded area during the arterial phase or during the venous phase.

In the event that on account of extreme AV parameters, no complete 3D subtraction image data record with a purely arterial or venous phase can be generated, the intermediate step described below is proposed. This is necessary for instance if only the first 60 recorded projection image data records map a purely arterial phase and an additional capillary phase or venous phase is then already shown.

In this case, the subtraction image data records are formed from all recorded projection image data records by deducting the corresponding native projection image data record. A projection image is selected therefrom, which contains a purely arterial phase. This selection can be automated by purely exemplary subtraction image data record number 10 being selected as a reference image data record from a purely exemplary subtraction image data record which was created from a projection image data record recording briefly following administration of the contrast agent, and the overall signal intensity is determined. This is essentially free of signals and the main contribution takes place by means of the contrast agent. This subtraction image data record is deducted from the following subtraction image data records in order to generate first intermediate image data records. In the intermediate image data records, the signal intensity of the pixels featuring a signal value below zero is totaled and compared with the overall signal intensity of the reference image data record. Once the negative signal values of an intermediate image data record essentially have the overall signal intensity of the reference image data record overall in terms of quantity, this means that the associated subtraction image was recorded at a phase, which connects directly to the arterial phase. The corresponding subtraction image is then used and is deducted from all originally generated subtraction images with a mixed phase for generating second intermediate image data records. The mixed phase exists in all images, which lie between the last image data record with a purely arterial phase and the subtraction image data record determined with the described method. In order to remain in the described example, this involves the subtraction image data records 61 to 159. In the second intermediate image data records thus generated, all pixels with a signal intensity below a predetermined threshold value, in particular all signal intensities below 0, are set to zero. The signal of the venous phase can be calculated in this way from the subtraction image data records 61 to 159.

A number of 3D subtraction image data records, which only map the arterial phase, can then be determined with the afore-described "sliding window" technique from the subtraction image data records 1 to 159 from consecutive subtraction image data records.

As described, this additional effort is however only required with extreme AV parameters.

If a long venous phase is to be expected, a measuring pause can be introduced during the measurement of the 3D image data record following administration of the contrast agent. This may amount to up to 2 s depending on the expected duration of the venous phase and is introduced after recording the first half of the projection image data records.

FIG. 2, and also the following figures, indicates the arterial and venous phase by filling the ellipses paths of the projection image data records following administration of the contrast agent, wherein the closely hatched surface displays the arterial phase and the widely hatched surface the venous phase. There is naturally no abrupt change in the phases, but instead a smooth transition.

For illustration purposes, FIG. 3 shows the "sliding window" technique, wherein it is assumed that the measurement of the projection image data records starts at an angle of 0°. The subtraction image data records n1 to n132 are used to generate the first 3D subtraction image data record n128 to n260 from the subtraction image data records are used to generate a further 3D subtraction image data record. All projection image data records disposed therebetween and recorded consecutively can likewise be used to generate 3D subtraction image data records. This is enabled by recording data across a large rotation angle.

It is particularly possible by means of the "sliding window" technique to display the passage of the contrast agent bolus through the arteries and the veins. In this way it is not only possible to generate static displays but also dynamic displays, as a result of which an improved diagnostic can be achieved.

Figure 4:
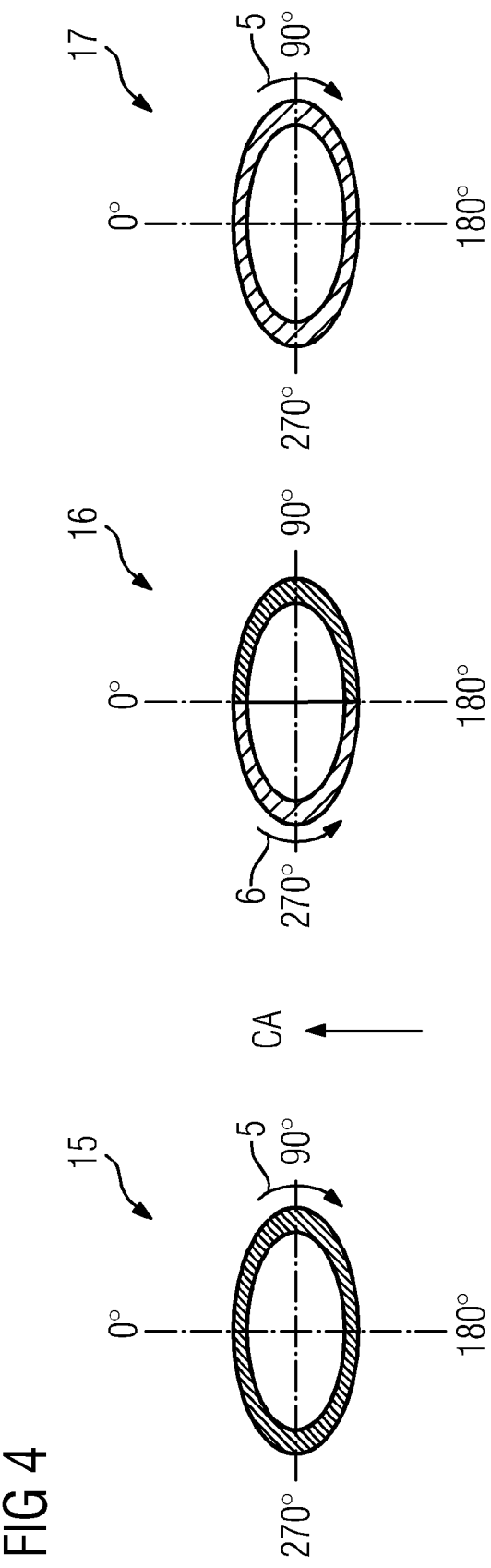
FIG. 4 shows a flow diagram of the method in a third embodiment and
FIG. 5 shows a flow diagram of the method in a fourth embodiment.

FIG. 4 shows an embodiment in the event that a longer lasting venous phase exists. A number of 3D image data records can then also be recorded following administration of the contrast agent. Their projection image data records are recorded through a rotation angle of 360°, wherein the recording directions are opposite. After recording the native 3D image data record 15, a contrast agent is provided and the 3D image data record 16 is then recorded. The 3D image data record 17 is then acquired again. The recording direction is changed in each instance therebetween, such as the arrows 5 and 6 indicate. As a result, the measurement can take place directly consecutively without measuring time loss. The reconstruction of the measuring data takes place as already described. Further 3D image data records can naturally still be recorded following administration of the contrast agent.

Figure 5:
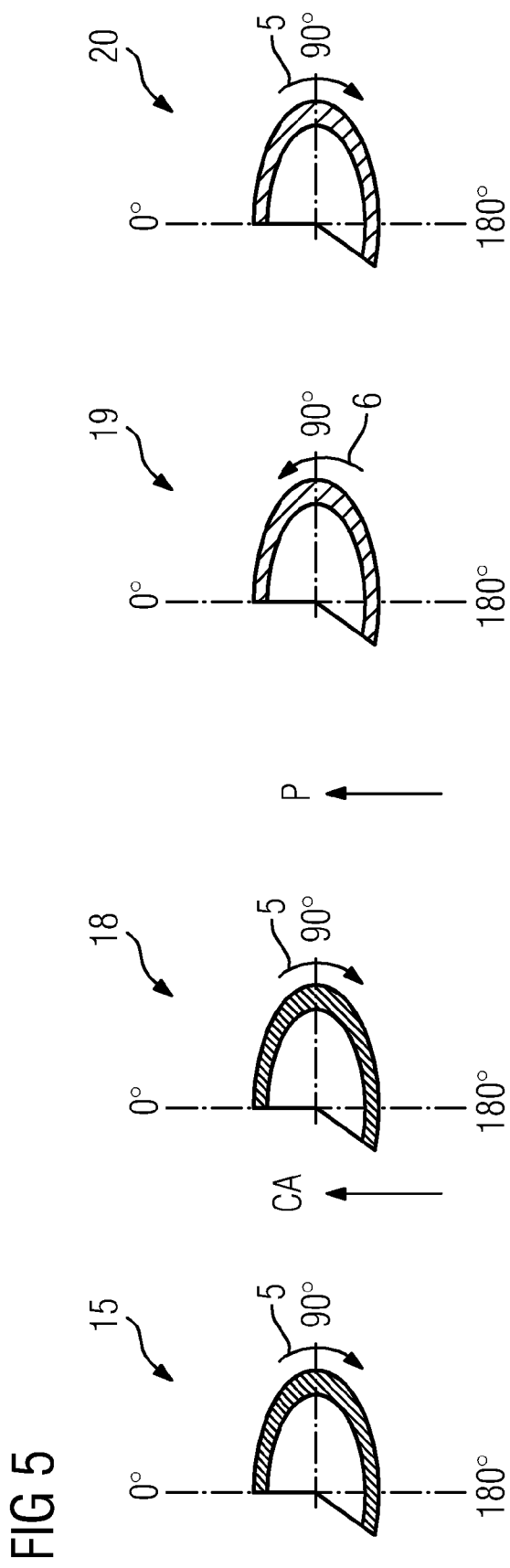

FIG. 5 shows an embodiment, in which only one rotation angle of 180° plus fan angle is used. Following administration of the contrast agent, at least two, in particular three 3D image data records are then recorded. After recording the native 3D image data record 15, the C-arm moves back into its starting position. The projection images of the 3D image data records 18, 19 and 20 recorded subsequently following administration of the contrast agent or the subtraction image data records are strung together in order to enable the generation of a plurality of 3D image data records with the afore-described "sliding window" technique. The 3D image data records 18 to 20 which can be generated as such can be registered with one another in order to create improved 3D subtraction images.

It is possible in all exemplary embodiments to perform an intravenous injection of the contrast agent instead of an intra-arterial injection and to initially record the venous phase and then the arterial phase in the projection image data records.

Furthermore, a measuring pause P can take place in all embodiments during the recording of a 3D image data record following administration of the contrast agent. This measuring pause is applied in the time frame in which a mixed phase, in other words the simultaneous presence of contrast agent in arteries and veins is to be expected. This measuring data is rejected with a high probability, as a result of which it is not even acquired to save on radiation dose.

While specific embodiments have been described in detail, those with ordinary skill in the art will appreciate that various modifications and alternative to those details could be developed in light of the overall teachings of the disclosure. For example, elements described in association with different embodiments may be combined. Accordingly, the particular arrangements disclosed are meant to be illustrative only and should not be construed as limiting the scope of the claims or disclosure, which are to be given the full breadth of the appended claims, and any and all equivalents thereof. It should be noted that the term "comprising" does not exclude other elements or steps and the use of articles "a" or "an" does not exclude a plurality.

The invention claimed is:

1. A method for recording and displaying at least two 3D subtraction image data records consisting of a native 3D image data record and a 3D image data record recorded following an administration of a contrast agent, wherein the at least two 3D subtraction image data records display at least a part of a vascular system of a patient, using a C-arm x-ray apparatus, wherein the 3D image data records are obtained from a predetermined number of two-dimensional projection image data records, comprising:
implementing a mask run by recording a predetermined number of mask run two-dimensional projection image data records with a rotation angle of at least 180° plus fan angle plus an additional angle,
implementing a filler run following administration of a contrast agent by recording a predetermined number of filler run two-dimensional projection image data records at the same angular positions of the mask run,
generating two-dimensional subtraction images by subtracting data of the mask run two-dimensional projection image data records from data of the filler run two-dimensional projection image data records,
generating at least two 3D subtraction image data record each by reconstructing a set of the two-dimensional subtraction images, and
displaying the at least two 3D subtraction image data records on a display apparatus,
wherein the additional angle is set depending on the predetermined number of two-dimensional projection image data records to be recorded minus a minimal number of two-dimensional projection image data records,
wherein the minimal number of two-dimensional projection image data records is recorded in a rotation angle of at least 180° plus the fan angle, and
wherein the at least two 3D subtraction image data record are generated for separately mapping an arterial phase and an venous phase of the vascular system of the patient.

2. The method as claimed in claim 1, wherein a rotation direction of a C-arm of a C-arm x-ray apparatus is changed between two rotation runs, and wherein the C-arm is not moved between rotation runs and does not return to a starting position of a previous rotation run.

3. The method as claimed in claim 1, wherein at least two filler rotation runs are performed following the administration of the contrast agent.

4. The method as claimed in claim 3, wherein a rotation angle of at least 270° is used for each of the at least two filler rotation runs, and wherein at least 180 projection image data records are recorded.

5. The method as claimed in claim 3, wherein a rotation angle of at least 350° is used for each of the at least two filler rotation runs, and wherein at least 240 projection image data records are recorded.

6. The method as claimed in claim 1, wherein, prior to a filler run, a 2-D-digital subtraction angiography is implemented, in which a sequence of projection images is recorded with high temporal resolution on which the inflow of a test bolus is visible, and wherein, based upon an inflow behavior of the test bolus on the projection images, at least one recording parameter of the filler run is determined.

7. The method as claimed in claim 6, wherein the at least one recording parameter is selected from the group consisting of a rotation speed, a recording density, a delay between injection of the contrast agent and start of the filler run, and a combination thereof.

8. The method as claimed in claim 1, wherein a biplanar C-arm x-ray apparatus is used.

9. The method as claimed in claim 1, wherein a C-arm x-ray apparatus with a stationary foot is used.

10. The method as claimed in claim 1, wherein a recording pause is introduced during the recording of the projection image data of at least one filler run.

11. The method as claimed in claim 10, wherein the recording pause, at a projection angle of at least 200°, is introduced from an angle at a start of the recording of the at least one filler run.

12. The method as claimed in claim 1, wherein the 3D subtraction image data records are shown using color coding, wherein arteries and veins are displayed using different colors.

13. The method as claimed in claim 1, wherein the 3D subtraction image data records are shown overlaid with a projection image data record of the mask run or a fluoroscopy image.

14. A C-arm x-ray apparatus, comprising:
a C-arm;
an x-ray source arranged on one end of the C-arm;
a detector arranged on another end of the C-arm that:
records a predetermined number of mask run two-dimensional projection image data records with a rotation angle of at least 180° plus fan angle plus an additional angle, and
records a predetermined number of filler run two-dimensional projection image data records at the same angular positions of the mask run following administration of a contrast agent;
a control apparatus that:
generates two-dimensional subtraction images by subtracting data of the mask run two-dimensional projection image data records from data of the filler run two-dimensional projection image data records, and generates at least two 3D subtraction image data records each by reconstructing a set of the two-dimensional subtraction images; and a display apparatus that displays the at least two 3D subtraction image data records on a display apparatus, wherein the additional angle is set depending on a predetermined number of two-dimensional projection image data records to be recorded minus a minimal number of two-dimensional projection image data records, wherein the minimal number of two-dimensional projection image data records is recorded in a rotation angle of at least 180° plus the fan angle, and wherein the at least two 3D subtraction image data record are generated for separately mapping an arterial phase and an venous phase of the vascular system of the patient.

15. A method for recording and displaying at least two 3D subtraction image data records consisting of a native 3D image data record and a 3D image data record recorded following an administration of a contrast agent, wherein the at least two 3D subtraction image data records display at least a part of a vascular system of a patient, using a C-arm x-ray apparatus, wherein the 3D image data records are obtained from a predetermined number of two-dimensional projection image data records, comprising:

implementing a mask run by recording a predetermined number of mask run two-dimensional projection image data records with a rotation angle of at least 180° plus fan angle plus an additional angle, implementing a filler run following administration of a contrast agent by recording a predetermined number of filler run two-dimensional projection image data records at the same angular positions of the mask run, generating native 3D image data records by reconstructing the mask run two-dimensional projection image data records, generating filler run 3D image data records by reconstructing the filler run two-dimensional projection image data records, generating at least two 3D subtraction image data records by subtracting one of the native 3D image data records from one of the filler run 3D image data records, and displaying the at least two 3D subtraction image data records on a display apparatus, wherein the additional angle is set depending on the predetermined number of two-dimensional projection image data records to be recorded minus a minimal number of two-dimensional projection image data records, wherein the minimal number of two-dimensional projection image data records is recorded in a rotation angle of at least 180° plus the fan angle, and wherein the at least two 3D subtraction image data record are generated for separately mapping an arterial phase and an venous phase of the vascular system of the patient.

* * * * *